United States Patent [19]

Corrigan

[11] Patent Number: 5,490,995
[45] Date of Patent: * Feb. 13, 1996

[54] SOLID NONDIGESTIBLE POLYOL POLYESTERS CONTAINING ESTERIFIED HYDROXY FATTY ACIDS SUCH AS ESTERIFIED RICINOLEIC ACID

[75] Inventor: Patrick J. Corrigan, Cincinnati, Ohio

[73] Assignee: The Procter & Gamble Company, Cincinnati, Ohio

[*] Notice: The portion of the term of this patent subsequent to Jan. 11, 2011, has been disclaimed.

[21] Appl. No.: 968,792

[22] Filed: Oct. 30, 1992

[51] Int. Cl.$^6$ ..................................................... A23L 1/00
[52] U.S. Cl. ........................... 426/531; 426/601; 426/611; 426/804; 536/119; 554/227
[58] Field of Search .................................. 426/438, 531, 426/549, 601, 606, 607, 609, 610, 611, 612, 804; 536/119; 554/161, 227

[56] References Cited

U.S. PATENT DOCUMENTS

| | | | |
|---|---|---|---|
| 2,266,591 | 12/1941 | Eckey et al. | 99/163 |
| 2,962,419 | 11/1960 | Minich | 167/81 |
| 3,059,009 | 10/1962 | Schmid et al. | 260/428 |
| 3,059,010 | 10/1962 | Schmid et al. | 260/428 |
| 3,093,481 | 6/1963 | Eckey et al. | 99/118 |
| 3,158,490 | 11/1964 | Baur et al. | 99/118 |
| 3,353,966 | 11/1967 | Hugenberg et al. | 99/163 |
| 3,353,967 | 11/1967 | Lutton | 99/163 |
| 3,495,010 | 2/1970 | Fossel | 424/312 |
| 3,495,011 | 2/1970 | Fossel | 424/312 |
| 3,600,186 | 8/1971 | Mattson et al. | 99/1 |
| 3,649,647 | 3/1972 | Ota | 260/345.8 |
| 4,005,195 | 1/1977 | Jandacek | 424/180 |
| 4,005,196 | 1/1977 | Jandacek et al. | 424/180 |
| 4,363,763 | 12/1982 | Peterson | 260/410.7 |
| 4,368,213 | 1/1983 | Hollenbach et al. | 426/590 |
| 4,469,635 | 9/1984 | Peterson | 260/403 |
| 4,582,715 | 4/1986 | Volpenhein | 426/601 |
| 4,797,300 | 1/1989 | Jandacek et al. | 426/549 |
| 4,830,787 | 5/1989 | Klemann | 260/410 |
| 4,959,465 | 9/1990 | Klemann | 536/115 |
| 4,963,386 | 10/1990 | Klemann | 426/611 |
| 5,017,398 | 5/1991 | Jandacek et al. | 426/603 |
| 5,085,884 | 2/1992 | Young et al. | 426/611 |
| 5,102,683 | 4/1992 | Letton et al. | 426/601 |
| 5,137,743 | 8/1992 | Zaks et al. | 426/602 |
| 5,158,796 | 10/1992 | Bernhardt et al. | 426/549 |
| 5,194,270 | 3/1993 | Cante et al. | 426/74 |
| 5,219,604 | 6/1993 | Klemann et al. | 426/531 |
| 5,225,049 | 7/1993 | Barmentlo et al. | 203/34 |
| 5,230,913 | 7/1993 | Klemann | 426/97 |
| 5,236,733 | 8/1993 | Zimmerman et al. | 426/611 |

FOREIGN PATENT DOCUMENTS

| | | | |
|---|---|---|---|
| 233856 | 8/1987 | European Pat. Off. | A23D 5/00 |
| 236288 | 9/1987 | European Pat. Off. | A23D 5/00 |
| 311154 | 4/1989 | European Pat. Off. | C07H 13/06 |
| 0325463 | 7/1989 | European Pat. Off. | C07C 69/675 |
| 390410 | 10/1990 | European Pat. Off. | A23D 9/00 |
| 424066 | 4/1991 | European Pat. Off. | C07H 13/06 |
| 434117 | 6/1991 | European Pat. Off. | C07H 13/06 |
| 434119 | 6/1991 | European Pat. Off. | C07H 13/06 |
| 227137 | 9/1985 | German Dem. Rep. | |
| 49-26220 | 3/1974 | Japan . | |
| 52-27694 | 7/1977 | Japan . | |
| 58-78531 | 5/1983 | Japan | A21D 2/16 |
| 9062511A | 4/1984 | Japan . | |
| 59-143550 | 8/1984 | Japan . | |
| 59-156242 | 9/1984 | Japan . | |
| 2020247A | 1/1990 | Japan . | |
| 2-262538 | 10/1990 | Japan | C07C 69/732 |
| 04237458A | 8/1992 | Japan | A23D 9/00 |
| 3-81042 | 8/1992 | Japan | A23D 9/00 |
| WO91/15961 | 10/1991 | WIPO | A23D 7/00 |
| WO91/15962 | 10/1991 | WIPO | A23D 9/00 |
| WO91/15963 | 10/1991 | WIPO | A23D 9/00 |
| WO91/15960 | 10/1991 | WIPO | A23D 7/00 |
| WO92/04360 | 3/1992 | WIPO | C07H 13/06 |
| 92/03937 | 3/1992 | WIPO | A23L 1/308 |
| 92/17077 | 10/1992 | WIPO | A23L 1/308 |

Primary Examiner—Leslie Wong
Attorney, Agent, or Firm—Tara M. Rosnell; G. W. Allen; Rose Ann Dabek

[57] ABSTRACT

Solid nondigestible polyol polyesters wherein the ester groups contain (1) fatty acid radicals having at least one hydroxyl group that is esterified with another fatty acid or other organic radical, and (2) at least about 15% long chain ($C_{20}$ or higher) saturated fatty acid radicals. The molar ratio of (1):(2) is from about 0.1:7.9 to about 3:5. These solid nondigestible polyol polyesters are very efficient passive oil loss control agents for liquid nondigestible oils. Edible fat-containing products including nondigestible fats containing these solid polyol polyesters can be less waxy tasting due to the lower level of solids required for passive oil loss control.

20 Claims, 1 Drawing Sheet

SOLID NONDIGESTIBLE POLYOL POLYESTERS CONTAINING ESTERIFIED HYDROXY FATTY ACIDS SUCH AS ESTERIFIED RICINOLEIC ACID

TECHNICAL FIELD

The present invention relates to novel, nondigestible, solid fat-like compounds that are useful as thickeners for liquid edible oils in formulating fluid cooking and salad oils or semi-solid oleaginous products such as shortening and margarines. The present invention further relates to blends of these nondigestible, solid fat-like compounds with liquid nondigestible oils to provide nondigestible fat compositions which exhibit passive oil loss control without being excessively waxy tasting.

BACKGROUND OF THE INVENTION

Certain polyol fatty acid polyesters have been suggested as low or reduced calorie substitutes for triglyceride fats and oils used in foods. For example, nonabsorbable, nondigestible sugar fatty acid esters or sugar alcohol fatty acid esters having at least 4 fatty acid ester groups with each fatty acid having from 8 to 22 carbon atoms have been used as partial or full fat replacers in low calorie food compositions. (See Mattson & Volpenhein; U.S. Pat. No. 3,600,186; Issued Aug. 17, 1971.) Foods in which these polyol polyesters are particularly useful as partial or complete replacements for triglyceride fats or oils include products suitable for use in frying. Unfortunately, regular ingestion of moderate to high levels of completely liquid forms of these polyol polyesters can produce undesirable passive oil loss, namely, leakage of the polyesters through the anal sphincter. By contrast, completely solid versions of these polyesters provide a sufficiently high solids content at mouth temperatures (e.g., 92° F., 33.3° C.) such that they give a waxy taste or impression in the mouth when ingested.

As an alternative to these completely liquid or completely solid nondigestible/nonabsorbable polyol polyesters, certain intermediate melting polyol fatty acid polyesters have been developed that provide passive oil loss control, while at the same time reducing waxiness in the mouth. (See Bernhardt; European Patent Application Nos. 236,288 and 233,856; Published Sep. 9, and Aug. 26, 1987, respectively.) These intermediate melting polyol polyesters exhibit a unique theology at body temperature by virtue of their having a matrix which involves a minimal level of solids (e.g. about 12% or lower) that bind the remaining liquid portion. As a result, these intermediate melting polyol polyesters are sufficiently viscous and have a sufficiently high liquid/solid stability at body temperature to provide passive oil loss control. An example of such intermediate melting polyol polyesters are those obtained by substantially completely esterifying sucrose with a 55:45 mixture of fully hydrogenated (hardstock) and partially hydrogenated soybean oil fatty acid methyl esters. (See Examples 1 and 2 of the above European patent applications.)

These intermediate melting polyol polyesters can be used as total or partial replacements for other fats and oils in various food products, including cooking and frying oils. However, it has been found that certain foods such as potato chips fried in frying fats containing substantial levels of these nondigestible intermediate melting polyol polyesters, particularly at levels in excess of about 40%, can give a significantly increased waxiness impression compared to potato chips that have been fried in the digestible triglyceride fat or oil that the nondigestible polyol polyester has partially replaced. (In terms of physical properties, "waxiness" relates to how the fat composition is sensed in the mouth, and specifically relates in part to the sensation of the product having a relatively high level of solids.) Indeed, this increased waxiness impression with regard to these intermediate melting polyol polyesters is recognized in the aforementioned European Patent Application No. 233,856 inasmuch as that application discloses fat compositions which contain digestible food materials, such as triglycerides and substituted mono- and diglycerides, that act as solvents for the intermediate melting polyol polyesters. However, as the proportion of triglycerides is increased relative to the intermediate melting polyol polyesters so as to impart less waxiness, the caloric content of the frying fat also increases accordingly. In addition, it has been found that frying fats containing greater than about 40% of these intermediate melting polyol polyesters can adversely affect the flavor display of the resulting fried food, in particular potato chips.

The waxiness impression imparted by intermediate melting polyol polyesters such as those of the aforementioned European '288 and '856 applications is believed to be due at least in part to their change in Solid Fat Content (SFC), particularly between typical room temperature (i.e. 70° F., 21.1° C.) and body temperature (i.e. 98.6°, 37° C.). For example, the intermediate melting sucrose polyester of Example 2 of European Patent Application Nos. 233,856 and 236,128 has an SFC profile slope (as hereinafter defined) between room temperature and body temperature of about −1.3. In other words, the SFC profile slope of these intermediate melting polyol polyesters is relatively steep. Given this relatively steep SFC profile slope, the change in solids content of these intermediate melting polyol polyesters can be sufficiently great such that a high level of solids will be sensed when such room temperature materials are first placed in the mouth, thereby leading to an increased waxiness sensation.

Blends of completely liquid polyol polyesters with completely solid polyol polyester hardstocks, preferably esterified with $C_{10}$–$C_{22}$ saturated fatty acids (e.g. sucrose octastearate), have also been proposed in order to provide passive oil loss control. (See, for example, Jandacek; U.S. Pat. No. 4,005,195; and Jandacek/Mattson; U.S. Pat. No. 4,005,196; Both issued Jan. 25, 1977.) Blends of these liquid polyol polyesters and solid polyol polyesters hardstocks have relatively flat SFC profile slopes between typical room temperature and body temperature, i.e. slopes of from 0 to about −0.3, and more typically from 0 to about −0.1. In other words, there is little or no change in the solids content of these blends between room temperature and body temperature.

Although providing at least temporary passive oil loss control, blends of liquid polyol polyesters and solid polyol polyester hardstocks according to the aforementioned U.S. '195 and '196 patents do not necessarily provide passive oil loss control over an extended period of time. It has been found that these solid polyol polyester hardstocks normally tend to form large spherulitic particles (typically from about 3 to about 32 microns in size) in the liquid polyol polyesters. These large spherulitic particles may tend to phase separate from the liquid polyol polyesters during storage of such blends. As a result, a two-phase system can develop with the liquid portion thereof providing minimal or no passive oil loss control.

In addition, blends of liquid polyol polyesters and solid polyol polyester hardstocks according to the aforementioned U.S. Pat. Nos. 4,005,195 and 4,005,196 do not necessarily lead to less waxy tasting products. As taught in these patents, a relatively high level of solid polyol polyester hardstock is required to provide passive oil loss control. For example, hardstock is preferably used in an amount of from about 20% to about 50% by weight of the liquid polyol polyester. (See Column 9, lines 65–68, of U.S. Pat. No. 4,005,195.) Such a level of solid polyol polyester hardstock used for passive oil loss control at body temperature can lead to a waxy tasting product due to the relatively high level of solids that will also be present at mouth temperature.

In view of the foregoing, it would be desirable to provide nondigestible fat compositions comprising blends of liquid polyol polyesters and solid polyol polyester hardstock particles with such blends exhibiting little or no phase separation of the hardstock particles from the liquid polyol polyesters. In addition, it would be desirable to be able to reduce the level of solid polyol polyester hardstock required for effective passive oil loss control so as to provide less waxy tasting products.

In addition to being useful as passive oil loss control agents when combined with liquid nondigestible oils, certain polyol polyesters which are solid at temperatures of about 25° C. and higher have also been used as thickening agents for conventional digestible triglyceride oils. For example, these solid polyol polyesters have been used as "thickening agents" for blending with liquid digestible or nondigestible oils in formulations such as shortenings, as well as in other food products which contain a combination of fat and non-fat ingredients, e.g., margarines, mayonnaise, frozen dairy desserts and the like. (See, for example, Jandacek and Letton; U.S. Pat. No. 4,797,300; Issued Jan. 10, 1989.) However, these prior art thickening agents had to be used at levels of 10 to 25%. Accordingly, it would also be desirable to reduce the level of thickening agents of this type in order to provide less waxy tasting products.

SUMMARY OF THE INVENTION

The present invention relates to novel nondigestible polyol polyesters having a complete melting point above about 25° C. In such polyol polyesters the polyol moiety has at least 4 hydroxyl groups with at least 4 of the hydroxyl groups being esterified. The ester groups in these polyol polyesters comprise a combination of: (i) at least about 15% $C_{20}$ and higher saturated fatty acid radicals, and (ii) fatty-fatty radicals which are fatty acid radicals having at least one hydroxyl group that is esterified with another fatty or organic acid radical. The average molar ratio of fatty-fatty acid radicals to long chain saturated fatty acid radicals ranges from about 0.1:7.9 to about 3:5.

The present invention also relates to nondigestible fat compositions useful as replacements for triglyceride fats or oils in foods. Such nondigestible fat compositions have a Solid Fat Content profile slope between 70° F. and 98.6° F. of between 0 and −0.75 % solids/°F. Such compositions comprise a liquid nondigestible oil having a complete melting point below about 37° C. in which are dispersed particles of certain of the hereinbefore described solid polyol polyester (those melting above about 37° C.). Such particles are dispersed in the liquid nondigestible oil in an amount sufficient to control passive oil loss upon ingestion of these nondigestible fat compositions.

The present invention also relates to digestible fat compositions which utilize particles of the hereinbefore described nondigestible polyol polyester material as thickening agents. Such compositions comprise from about 85% to about 99% of a digestible edible oil and from about 1% to about 15% of the nondigestible solid polyol polyester particles.

The solid polyol polyesters of the present invention provide significant advantages over prior thickening agents because they cause liquid digestible or nondigestible oils to thicken when used at very low levels. For example because they cause liquid oils to gel at such low levels, these solid polyol polyesters provide especially efficient passive oil loss control when blended with liquid nondigestible oils. Also, as a result of the low level of solids required for thickening of liquid oils, the use of the solid polyol polyesters of the present invention can result in less waxy tasting products containing these solid polyol polyesters.

DETAILED DESCRIPTION OF THE INVENTION

A. Definitions

Figure 1:
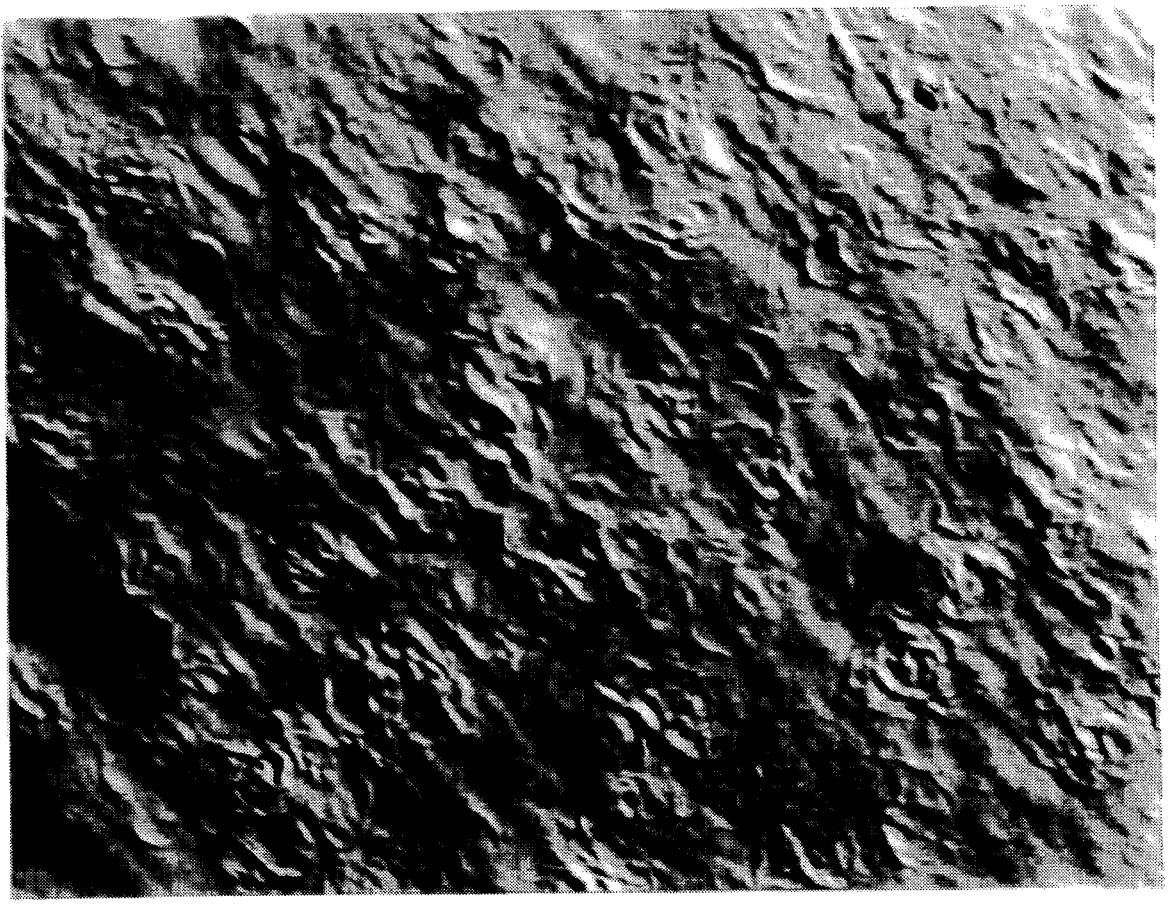
FIG. 1 is a photomicrograph (magnification of 1,000×) depicting particles of a solid polyol polyester containing ester groups formed from fatty-fatty acid radicals dispersed in a liquid sucrose polyester.

By "nondigestible" is meant that only about 70% or less of a material so characterized can be digested by the body. Preferably only about 20% or less of such materials can be digested. More preferably only about 1% or less of such materials can be digested.

As used herein, the term "thickness" is used in its conventional sense of the smallest of three dimensions (length, width, height) of any given particle.

As used herein, the term "spherulitic" refers to substantially spherical or round, essentially three-dimensional particles.

As used herein, the term "platelet-like" refers to a substantially flat, essentially two-dimensional type of particle having length and width in the unfolded planar configuration that is substantially greater in dimension than its thickness.

As used herein, the terms "filament-like" and "platelet-like" refer to elongated, essentially one-dimensional particles.

As used herein, the term "complete melting point" refers to the temperature at which all solid components have melted. All melting points referred to herein are measure by Differential Scanning Calorimetry (DSC) as described hereinafter.

As used herein, the term "comprising" means various components, or steps, can be conjointly employed in the nondigestible fats, compositions, and processes of the present invention. Accordingly, the term "comprising" encompasses the more restrictive terms "consisting essentially of" and "consisting of".

By "polyol" is meant a polyhydric alcohol containing at least 4, preferably from 4 to 12, more preferably from 4 to 8, most preferably from 6 to 8, hydroxyl groups. Polyols thus include sugars (i.e., monosaccharides, disaccharides and trisaccharides), sugar alcohols (i.e., the reduction product of sugars wherein the aldehyde or ketone group has been reduced to an alcohol), other sugar derivatives (e.g., alkyl glycosides), polyglycerols such as diglycerol and triglycerol, pentaerythritol, and polyvinyl alcohols. Specific examples of suitable sugars, sugar alcohols, and sugar derivatives include xylose, arabinose, ribose, xylitol, erythritol, glucose, methyl glucoside, mannose, galactose, fructose, sorbitol, maltose, lactose, sucrose, raffinose, and maltotriose. Preferred polyols include erythritol, xylitol, sorbitol, and glucose, with sucrose being an especially preferred polyol.

By "polyol polyester" is meant a polyol having at least 4 fatty acid ester groups, i.e., at least 4 of the hydroxyl groups are esterified with fatty or other organic acids. Polyol esters that contain 3 or less ester groups are digested in (and the products of digestion are absorbed from) the intestinal tract much in the manner of ordinary triglyceride fats or oils, whereas those polyol esters containing 4 or more ester groups are generally substantially nondigestible and consequently nonabsorbable by the human body. It is not necessary that all of the hydroxyl groups of the polyol be esterified, but it is preferable that disaccharide molecules contain no more than 3 unesterified hydroxyl groups, and more preferably no more than 2 unesterified hydroxyl groups, so that they are rendered nondigestible. Typically, substantially all (e.g., at least about 85%) of the hydroxyl groups of the polyol are esterified. For liquid polyol polyesters, preferably at least about 95% of the hydroxyl groups of the polyol are esterified. In the case of sucrose polyesters, typically from about 7 to 8 of the hydroxyl groups of the polyol are esterified.

By "ester group" is meant a moiety formed from the reaction of a hydroxyl group with an organic acid or acid derivative, which moiety contains fatty acid and/or other organic radicals having at least 2 carbon atoms, typically at least 8 carbon atoms, more typically at least 12 carbon atoms, most typically at least 16 carbon atoms. Representative examples of such fatty acid and other organic radicals include acetic, propionic, butyric, caprylic, capric, lauric, myristic, myristoleic, palmitic, palmitoleic, stearic, oleic, elaidic, ricinoleic (hydroxyl group unesterified or esterified with fatty or other organic acids), linoleic, linolenic, eleostearic, arachidic, arachidonic, behenic, lignoceric, erucic, and cerotic fatty acid radicals and other organic radicals including aromatic esters such as benzoic or toluic; branched chain radicals such as isobutyric, neooctanoic or methyl stearic; ultra-long chain saturated or unsaturated fatty acid radicals such as tricosanoic or tricosenoic; cyclic aliphatics such as cyclohexane carboxylic; and polymeric ester-forming radicals such as polyacrylic or dimer fatty acid. These fatty or other organic acid radicals can be derived from naturally occurring or synthetic acids. The acid radicals can be saturated or unsaturated, including positional or geometric isomers, e.g. cis- or trans-isomers, straight chain or branched chain aliphatic or aromatic, and can be the same for all ester groups, or can be mixtures of different acid radicals.

All percentages and proportions are by weight, unless otherwise indicated.

B. Nondigestible Polyol Polyesters Containing Ester Groups Formed from Fatty-Fatty Acid Radicals The novel nondigestible polyol polyesters of the present invention are polyol polyesters which have a melting point above about 25° C. (preferably above 37° C., more preferably above about 50° C., most preferably above about 60° C.). Generally, these polyol polyesters contain two basic types of ester groups. These are (i) groups formed from certain long chain saturated fatty acid radicals, and (ii) groups formed from fatty-fatty acid radicals. The molar ratio of fatty-fatty acid radicals to long chain saturated fatty acid radicals is from about 0.1:7.9 to about 3:5, preferably about 0.5:7.5 to about 1.75:6.25, more preferably about 1:7 to about 1.5:6.5. A typical suitable molar ratio of fatty-fatty acid radicals to long chain saturated fatty acid radicals is about 1:7.

a) Long Chain Saturated Fatty Acid Component of the Solid Polyol Polyester Oil Loss Control Particles The ester groups of the solid polyol polyesters of the present invention must include those formed from certain long chain saturated fatty acid radicals. In particular, the ester groups should comprise at least about 15%, preferably at least 30%, more preferably at least 50%, most preferably at least 80% long chain saturated fatty acid radicals. Suitable long chain saturated fatty acid radicals comprise those which contain at least 20 carbon atoms, preferably from 20 to 26 carbon atoms, most preferably 22 carbon atoms. The long chain saturated fatty acid radicals can be used singly, or in mixtures with each other, in all proportions. In addition, straight chain (i.e., normal) fatty acid radicals are typically used as the long chain saturated fatty acid radicals which form ester groups on the solid polyol polyesters herein. Examples of suitable long chain saturated fatty acid radicals are palmitate, stearate, eicosanoate (arachidate), docosanoate (behenate), tetracosanoate (lignocerate), and hexacosanoate (cerotate).

b) Fatty-Fatty Acid Component of the Solid Polyol Polyester Oil Loss Control Particles The ester groups of the solid polyol polyester herein must also include those formed from fatty-fatty acid radicals. As used herein, the term "fatty-fatty acid radical" refers to a fatty acid radical having at least one hydroxyl group that is esterified with another fatty or other organic acid.

Examples of fatty acids containing a hydroxyl group that can be esterified with another fatty or other organic acid to form a fatty-fatty acid radical include 12-hydroxy-9-octadecenoic acid (ricinoleic acid), 12-hydroxy-octadecanoic acid, 9-hydroxyoctadecanoic acid, 9-hydroxy-10,12-octadecadienoic acid, 9-hydroxy-octadecanoic, 9,10-dihydroxydocosanoic acid, 15,16-dihydroxytetraconsanoic acid, 9,10-dihydroxyoctadecanoic acid, 12,12-dihydroxyeicosanoic acid, and 18-hydroxy- 9,11,13-octadecatrienoic acid (kamolenic acid). Ricinoleic acid is a preferred hydroxy-fatty acid. Castor oil is a convenient source of ricinoleic acid. Other sources of hydroxy-fatty acids include hydrogenated castor oil, strophanthus seed oils, calendula officinalis seed oils, hydrogenated strophanthus seed oils and hydrogenated calendula officinalis seed oils, cardamine impatiens seed oils, kamala oils, mallotus discolor oils, and reallotus claoxyloides oils.

Hydroxy fatty acids can also be synthetically prepared by oxidative hydroxylation of unsaturated fatty acids using oxidizing agents such as potassium permanganate, osmium tetroxide, and peracids such as peracetic acid. Using this method, 9,10-dihydroxy-octadecanoic acid can be made from oleic acid, and 9,10,12,13 -tetrahyxroxy-octadecanoic acid can be made from linoleic acid. Another way to prepare hydroxy fatty acids, such as 10-hydroxy-12-cis-octadecenoic and 10-hydroxy-12-cis, 15-cis-octadecactenoic acids, synthetically is by conversion of fatty acids such as linoleic and linolenic via microorganisms such as Nocardia Cholesteroliciim.

Suitable ester groups for esterification onto the hydroxyl group of the hydroxy-fatty acid radical can be derived from either synthetic or natural, saturated or unsaturated fatty and other organic acids and include positional and geometric isomers. Suitable preferred saturated fatty acids include, for example, acetic, butyric, caproic, caprylic, capric, lauric, myristic, palmitic, stearic, arachidic, behenic, isomyristic, isomargaric, and hydroxystearic. Suitable preferred unsaturated fatty acids for preparation of the fatty-fatty acid radicals include, for example, myristoleic, palmitoleic, ricinoleic, linoleic, oleic, elaidic, linolenic, eleostearic, arachidonic, erucic, and erythrogenic acids. Mixtures of fatty acids derived from soybean oil, palm oil, cottonseed oil, safflower oil, rapeseed oil (high erucic acid), canola (low erucic acid), and corn oil are especially preferred for preparation of the fatty-fatty acid radicals. The fatty acids can be used "as is" and/or after hydrogenation, and/or isomerization, and/or purification. For example, rapeseed provides a good source for $C_{22}$ fatty acid. $C_{16}$–$C_{18}$ fatty acids can be provided by tallow, soybean oil, or cottonseed oil. Shorter chain fatty acids can be provided by coconut, palm kernel, or babassu oils. Corn oil, lard, olive oil, palm oil, peanut oil, castor oil, safflower seed oil, sesame seed oil, and sunflower seed oil are examples of other natural oils which can serve as the source of these fatty acids that are esterified onto the hydroxyl group of the hydroxy-fatty acid radical.

Other suitable organic radicals for esterification onto the fatty acid radical containing the hydroxyl group to thereby form fatty-fatty acid radicals include aromatic esters such as benzoic or toluic; branched chain radicals such as isobutyric, neooctanoic or methyl stearic; ultra-long chain saturated or unsaturated fatty acids such as tricosanoic or tricosenoic; cyclic aliphatics such as cyclohexane carboxylic; and polymeric ester-forming radicals such as polyacrylic and dimer fatty acid.

The fatty-fatty radicals can be prepared prior to esterification onto the polyol by transesterifying the hydroxy group with the respective fatty acids or fatty acid esters. For example, fatty-fatty radicals of ricinoleic chains can be prepared by esterifying ricinoleic methyl ester with behenic methyl esters. Preferably, an excess of behenic methyl esters is used so that the majority of ricinoleic 12-hydroxy groups are esterified with behenic chains.

A more convenient method of preparing the fatty-fatty radicals is to prepare them in situ before, or preferably during, the esterification of the polyol. For example, one equivalent of sucrose, 1 equivalent of castor oil methyl esters, and 7 equivalents of methyl esters made from hydrogenated and distilled high erucic rapeseed methyl esters could be reacted together, along with a functional amount of emulsifier and basic catalyst. When these ingredients are heated under a vacuum, the esterification of the hydroxy fatty methyl esters (primarily ricinoleic methyl esters) will occur at about the same time as the transesterification of the fatty acid methyl esters with the sucrose. Since the majority of the fatty acid methyl esters are behenic methyl esters in this example, most of the 12-hydroxy groups on the ricinoleic methyl esters will esterify with the behenic methyl esters.

c). Preparation of the Solid Polyol Polyesters Containing Fatty-Fatty Acid Radicals The solid polyol polyesters hereinbefore described can be prepared by esterifying the desired polyol with the requisite type of ester-forming radicals. Mixed fatty acid radicals from oils which contain substantial amounts of the long chain saturated or hydroxy fatty acids can be used as sources of fatty acid radicals in preparing compounds of the invention. The mixed fatty acids from the oils should contain at least about 30% (preferably at least about 50%, and most preferably at least about 80%) of the desired fatty acids. For example, hardened (i.e., hydrogenated) high erucic rapeseed oil fatty acids can be used in place of a mixture of the respective pure long chain saturated fatty acids having from 20 to 26 carbon atoms. Preferably the $C_{20}$ and higher acids (or their derivatives—e.g., methyl esters) are concentrated, for example by distillation.

The solid polyol polyesters herein can be made according to prior known methods of preparing polyol polyesters. Since the sucrose polyesters are the preferred solid polyol polyesters for use in the present invention, such preparation will be exemplified primarily by these materials. One such method of preparation comprises reacting the acid chlorides or acid anhydrides of the desired ester-forming acids, or the acids per se, with sucrose, preferably using a sequential esterification process. In this sequential esterification process, sucrose is initially partially esterified with the hydroxy fatty acid chlorides, followed by complete or substantially complete esterification of this initial reaction product with the long chain saturated fatty acid chlorides, in that order, or in reverse order. (See Letton; European Patent 311,154; Published Apr. 12, 1989, herein incorporated by reference).

Another method of preparation comprises the process of reacting the methyl esters of the desired ester-forming acids acids with sucrose in the presence of a fatty acid soap and a basic catalyst such as potassium carbonate. (See, for example, Jandacek et al; U.S. Pat. No. 4,797,300; Issued Jan. 10, 1989; Rizzi et al; U.S. Pat. No. 3,963,699; Issued Jun. 15, 1976; Volpenhein: U.S. Pat. No. 4,518,772; Issued May 21, 1985; Volpenhein; U.S. Pat. No. 4,517,360; Issued May 14, 1985; and Letton; European Patent 311,154; Published Apr. 12, 1989, all of which are incorporated herein by reference.)

When the methyl ester route is used to prepare the solid polyol polyesters of the claimed invention, the reaction can also be run in two stages, with part of the fatty acid methyl esters added in the first stage, and part of the fatty acid methyl esters in the second stage. The first stage of the reaction is continued until most, or preferably all, of the sucrose has been converted to sucrose lower esters. The fatty acid methyl esters in the first and second stages of the reaction can be a mixture of hydroxy fatty acid methyl esters along with other methyl esters such as behenic methyl esters. Alternatively, the fatty acid methyl esters in the first stage can contain no hydroxy fatty acid methyl esters, with the hydroxy fatty acid methyl esters being added during the second stage of the reaction. Another alternative is to divide the reaction into three stages and, for example, adding part of the behenic methyl esters in the first stage, more behenic esters in the second stage, and the hydroxy fatty acid methyl esters (along with any remaining behenic methyl esters) in the third stage.

C. Nondigestible Fat Compositions Containing the Solid Polyol Polyesters Herein

The high capacity of the solid polyol polyesters herein to thicken liquid oils makes certain compounds of the present invention having a melting point above body temperature (37° C.) particularly useful in the formulation of food products containing liquid nondigestible oils so as to control or prevent the passive oil loss problem associated with the ingestion of such oils. Therefore, this invention also relates to nondigestible fat compositions useful as a replacement for triglyceride fats or oils in foods. These nondigestible fat compositions comprise:

A. a liquid nondigestible oil having a complete melting point below about 37° C.; and B. nondigestible solid particles of the polyol polyesters of the present invention dispersed in said oil in an amount sufficient to control passive oil loss upon ingestion of said composition, said polyol polyester particles having a complete melting point above about 37° C.

1) Liquid Nondigestible Oil Component of the Nondigestible Fat Compositions Herein A key component of the nondigestible fat compositions herein is a liquid nondigestible oil having a complete melting point below 37° C. Suitable nondigestible edible oils for use herein include liquid polyol polyesters (see Jandacek; U.S. Pat. No. 4,005,195; Issued Jan. 25, 1977); liquid esters of tricarballylic acids (Hamm; U.S. Pat. No. 4,508,746; Issued Apr. 2, 1985); liquid diesters of dicarboxylic acids such as derivatives of malonic and succinic acid (Fulcher; U.S. Pat. No. 4,582,927; Issued Apr. 15, 1986); liquid triglycerides of alpha-branched chain carboxylic acids (Whyte; U.S. Pat. No. 3,579,548; Issued May 18, 1971); liquid ethers and ether esters containing the neopentyl moiety (Minich; U.S. Pat. No. 2,962,419; Issued Nov. 29, 1960); liquid fatty polyethers of polyglycerol (Hunter et al; U.S. Pat. No. 3,932,532; Issued Jan. 13, 1976); liquid alkyl glycoside polyesters (Meyer et al; U.S. Pat. No. 4,840,815; Issued Jun. 20, 1989); liquid polyesters of two ether-linked hydroxycarboxylic acids (e.g., citric or isocitric) (Huhn et al; U.S. Pat. No. 4,888,195; Issued Dec. 19, 1988); liquid esters of epoxide-extended polyols (White et al; U.S. Pat. No. 4,861,613; Issued Aug. 29, 1989); as well as liquid polydimethyl siloxanes (e.g., Fluid Silicones available from Dow-Corning Corporation). All of the foregoing patents relating to the liquid nondigestible oil component are incorporated herein by reference.

Preferred liquid nondigestible oils are the liquid polyol polyesters that comprise liquid sugar polyesters, liquid sugar alcohol polyesters, and mixtures thereof. The preferred sugars and sugar alcohols for preparing these liquid polyol polyesters include erythritol, xylitol, sorbitol, and glucose, with sucrose being especially preferred. The sugar or sugar alcohol starting materials for these liquid polyol polyesters are preferably esterified with fatty acids containing from 8 to 22 carbon atoms, and most preferably from 8 to 18 carbon atoms. Suitable naturally occurring sources of such fatty acids include corn oil fatty acids, cottonseed oil fatty acids, peanut oil fatty acids, soybean oil fatty acids, canola oil fatty acids (i.e., fatty acids derived from low erucic acid rapeseed oil), sunflower seed oil fatty acids, sesame seed oil fatty acids, safflower oil fatty acids, fractionated palm oil fatty acids, palm kernel oil fatty acids, coconut oil fatty acids, tallow fatty acids and lard fatty acids.

The polyol fatty acid polyesters that are liquid are those which have minimal or no solids at body temperatures (i.e., 98.6° F., 37° C.). These liquid polyol polyesters typically contain ester groups having a high proportion of $C_{12}$ or lower fatty acid radicals or else a high proportion of $C_{18}$ or higher unsaturated fatty acid radicals. In the case of those liquid polyol polyesters having high proportions of unsaturated $C_{18}$ or higher fatty acid radicals, at least about half of the fatty acids incorporated into the polyester molecule are typically unsaturated. Preferred unsaturated fatty acids in such liquid polyol polyesters are oleic acid, linoleic acid, and mixtures thereof.

The following are nonlimiting examples of specific liquid polyol polyesters suitable for use in the present invention: sucrose tetraoleate, sucrose pentaoleate, sucrose hexaoleate, sucrose heptaoleate, sucrose octaoleate, sucrose hepta- and octaesters of unsaturated soybean oil fatty acids, canola oil fatty acids, cottonseed oil fatty acids, corn oil fatty acids, peanut oil fatty acids, palm kernel oil fatty acids, or coconut oil fatty acids, glucose tetraoleate, the glucose tetraesters of coconut oil or unsaturated soybean oil fatty acids, the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

The liquid polyol polyesters suitable for use herein can be prepared by a variety of methods known to those skilled in the art. These methods include: transesterification of the polyol (i.e. sugar or sugar alcohol) with methyl, ethyl or glycerol esters containing the desired acid radicals using a variety of catalysts; acylation of the polyol with an acid chloride; acylation of the polyol with an acid anhydride; and acylation of the polyol with the desired acid, per se. (See, for example, U.S. Pat. Nos. 2,831,854, 3,600,186, 3,963,699, 4,517,360 and 4,518,772, all of which are incorporated by reference. These patents all disclose suitable methods for preparing polyol fatty acid polyesters.)

2) Polyol Polyester Particles Component of the Nondigestible Fat Compositions Herein A second key component of the nondigestible fat compositions of this invention comprises relatively small nondigestible solid particles of certain of the polyol polyester materials hereinbefore described. These particles are dispersed in the liquid nondigestible oil to control or prevent passive oil loss. These particles can be in a variety of forms and shapes, including spherulitic, platelet-like, filament-like, or rod-like, or combinations of these various shapes, but are typically spherulitic or platelet-like. The thickness of these particles is typically about 1 micron or less. Thinner particles, however, are preferred from a standpoint of providing more efficient passive oil loss control of the liquid nondigestible oil component of the compositions herein. Accordingly, these particles preferably have a thickness of 0.1 micron or less, more preferably 0.05 micron or less. These particles also have a complete melting point above about 37° C., preferably, such solid above about 50° C., more preferably above about 60° C.

The polyol polyester material which forms these nondigestible particles should have a complete melting point as measured by the Differential Scanning Calorimetry (DSC) described hereinafter in the Analytical Methods section which is sufficiently high such that the nondigestible particles themselves will have the hereinbefore specified melting point characteristics when such particles are dispersed in the liquid nondigestible oil. For example, a polyol polyester material having a complete melting point right at 37° C. may not form solid particles having a complete melting point above about 37° C. when such particles are dispersed in the liquid nondigestible oil. Thus, in some cases, the complete melting point of the neat polyol polyester material may have to be slightly higher than 37° C., e.g., about 40° C. or higher, in order to form solid particles having a complete melting point of 37° C. when such particles are combined with the liquid nondigestible oil.

These nondigestible particles can generally be dispersed as discrete, unaggregated entities in the liquid nondigestible oil. However, these nondigestible particles can also cluster together to form much larger aggregates which are dispersed in the liquid nondigestible oil. This is particularly true of those nondigestible particles that are platelet-like in form. Aggregates of platelet-like nondigestible particles typically assume a spherulitic shape that is porous in character and thus capable of entrapping significant amounts of liquid nondigestible oil. It is believed that this porous structure and its concomitant ability to entrap large amounts of liquid nondigestible oil is why these aggregated, platelet-like particles, while not as efficient as the particles in unaggregated form, can provide very effective and efficient passive oil loss control.

The polyol polyester material which forms the solid particles used in the fat compositions herein generally comprises those of the solid polyol polyesters hereinbefore described which have a complete melting point above about 37° C.

D. Preparation of Nondigestible Fat Compositions Which Exhibit Minimum Passive Oil To prepare the nondigestible fat compositions herein which exhibit minimal passive oil loss, the liquid nondigestible oil is combined with particles of the solid polyol polyesters hereinbefore described. The polyol polyester particles are used in an amount sufficient to control passive oil loss. What constitutes "an amount sufficient to control passive oil loss" for any given fat composition depends on the particular solid polyol polyester utilized therein, the particular passive oil loss control benefits desired, and the level of waxiness mouth impressions which can be tolerated for the particular end product use of the nondigestible fat composition which is formulated. Typically, the nondigestible fat composition so formed will comprise from about 60% to about 99% of the liquid nondigestible oil and from about 1% to about 40% of the solid polyol polyester particles. Preferably, this mixture comprises from about 80% to about 99% liquid nondigestible oil and from about 1% to about 20% of the solid polyol polyester particles, more preferably from about 85% to about 99% liquid nondigestible oil and from about 1% to about 15% of the solid polyol polyester particles, even more preferably from about 90% to about 99% liquid nondigestible oil and from about 1% to about 10% of the solid polyol polyester particles, and most preferably from about 95% to about 99% liquid nondigestible oil and from about 1% to about 5% of the solid polyol polyester particles. The use of higher levels of liquid nondigestible oil (i.e., lower levels of solid polyol polyester particles) can be desirable from the standpoint of reducing the waxiness impression left by the solid components of the nondigestible fat compositions herein. However, higher levels of solid polyol polyester particles (i.e., lower levels of liquid nondigestible oil) can be desirable from the standpoint of controlling or preventing passive oil loss associated with the ingestion of compositions containing such liquid nondigestible oils.

This combination of liquid nondigestible oil and solid polyol polyester is typically formed by simply mixing the liquid and solid components together, by heating the mixture until the solid polyol polyester material dissolves in the oil, and then by cooling the mixture to a suitable crystallization temperature, e.g., room temperature which causes polyol polyester particles to form.

The specific size of the polyol polyester particles formed in the fat compositions herein will be dependent upon the rate at which the heated combination of oil and dissolved solid is cooled. As used herein, cooling rate is defined as the temperature differential between (a) the heated oil/dissolved solid combination and (b) the cooled crystallized liquid/solid particle combination, divided by the time taken to create this temperature differential. Generally the greater the cooling rate employed in forming the fat compositions herein, the smaller will be the particles of solid polyol polyester material dispersed in such compositions. Desirable cooling rates for use in forming the fat compositions herein are typically greater than 0.6° C./min. (1° F./min.), preferably greater than 2.8° C./min. (5° F./min.), more preferably greater than 5.6° C./min. (10° F./min.), and most preferably greater than 27.8° C./min. (50° F./min.). When the nondigestible fat compositions herein are to be formed in situ, for example, within a food product of which they form a part, then the type and concentration of the fat composition components should be selected so that the cooling profile experienced by the food product will result in formulation of the desired amount and size of the solid polyol polyester particles within the food product.

The formation of thin nondigestible particles according to the present invention provides especially efficient passive oil loss control for the resulting fat composition. Such efficiency permits a reduction in solids content of the nondigestible fat to relatively low levels (e.g., to from about 1% to about 15%). This reduction in solids levels required for passive oil loss control, together with the minimal/no change in solids between typical room and body temperatures, leads to nondigestible fats having a less waxy tasting impression.

Both the liquid nondigestible oil and the solid nondigestible polyol polyester components, as well as the respective concentrations, are selected in order to provide nondigestible fat compositions having a certain set of physical characteristics. In particular, the nondigestible fats of the present invention should exhibit a relatively flat Solid Fat Content (SFC) profile slope across the temperature range of from typical room temperature to body temperature, i.e., from 70° F. to 98.6° F. The SFC profile slope between these temperatures should be from 0 to about $-0.75\%$ solids/°F., preferably from 0 to about $-0.5\%$ solids/°F., more preferably from 0 to about $-0.3\%$ solids/°F., and most preferably from 0 to about $-0.1\%$ solids/°F. The method for determining the SFC profile slope of the fat compositions herein is described hereinafter in the Analytical Methods section.

E. Use of Nondigestible Fat Compositions in Edible Fat-Containing Food Products

The nondigestible fat compositions of the present invention can be used in various edible fat-containing product including foods, beverages and pharmaceuticals, either alone or in combination with other materials such as nondigestible or digestible fats and oils. In particular, the nondigestible fats of the present invention can be optionally formulated with a digestible triglyceride fat or oil. Generally, these formulations can comprise from about 10% to 100% nondigestible fat and from 0% to about 90% digestible triglyceride fat or oil. Preferably, these formulations comprise from 35% to 100%, more preferably from about 50% to about 100% and most preferably from about 75% to about 100% nondigestible fat, and from 0% to about 65%, more preferably from 0% to about 50%, and most preferably from 0% to about 25%, digestible triglyceride fat or oil. Because of the potential caloric impact of these triglyceride fats or oils, it is desirable to minimize the level at which they are combined with the nondigestible fats of the present invention.

As used herein, the term "triglyceride oil" refers to those triglyceride compositions which are fluid or liquid above about 25° C. Although not a requirement, the triglyceride oils useful in the present invention can include those which are fluid or liquid below 25° C. These triglyceride oils consist primarily of triglyceride materials, but can also include residual levels of other components such as mono- and diglycerides. To remain fluid or liquid at temperatures below 25° C., the triglyceride oil contains a minimal amount of glycerides having melting points higher than about 25° C. so as to limit the solids increase when the triglyceride oil is cooled. It is desirable that the triglyceride oil be chemically stable and resistant to oxidation.

Suitable triglyceride oils can be derived from naturally occurring liquid vegetable oils such as cottonseed oil, soybean oil, safflower oil, corn oil, olive oil, coconut oil, palm kernel oil, peanut oil, rapeseed oil, canola oil (i.e., rapeseed oil low in erucic acid), sesame seed oil, sunflower seed oil, and mixtures thereof. Also suitable are liquid oil fractions obtained from palm oil, lard and tallow by, for example, graining or directed interesterification, followed by separation of the oils. Oils predominating in glycerides of unsaturated acids can need some hydrogenation to maintain flavor, but care should be taken not to greatly increase the amount of glycerides melting above 25° C. When oils are selected which have a larger amount of solids melting between 25° and 40° C. than are desirable, it can be necessary to separate out the solids. For example, refined and slightly hydrogenated soybean oil is suitable, as well as refined cottonseed oil.

As used herein, the term "triglyceride fat" refers to those triglyceride compositions which are solid or plastic above about 25° C. These solid or plastic fats can be derived from plants or animals or can be edible synthetic fats or oils. For example, animal fats such as lard, tallow, oleo oil, oleo stock, oleo stearin and the like which are solid at room temperature can be utilized. Also, triglyceride oils, e.g. unsaturated vegetable oils, can be converted into plastic fats by partial hydrogenation of the unsaturated double bonds of fatty acid constituents of the oil followed by conventional chilling and crystallization techniques or by proper mixture with sufficient triglycerides which are solid at room temperature to form a rigid interlocking crystalline structure which interferes with the free-flowing properties of the liquid oil. See Purves et al; U.S. Pat. No. 3,355,302; Issued Nov. 28, 1967, and Darragh et al; U.S. Pat. No. 3,867,556; Issued Feb. 18, 1975 (herein incorporated by reference), for further examples of solid or plastic fats. Because the solid or plastic fats add an appreciable level of solids, their inclusion can cause adverse effects on the organoleptic properties, in particular waxiness, of the edible fat-containing products of the present invention.

Triglyceride fats and oils useful in the nondigestible fats of the present invention can include certain triglycerides in which one, two or three of the OH groups of the glycerol molecule have been substituted with acetyl, propionyl, butyryl, caproyl, caprylyl, or capryl radicals, and the remaining OH groups of the glycerol molecule (if any) have been substituted with acyl radicals of saturated or unsaturated fatty acids having from 12 to 24 carbon atoms.

The nondigestible fat materials of this invention can also be used in combination with reduced calorie medium chain and mixed medium/long chain triglycerides. See, for example, Ehrman et al.; U.S. Pat. No. 4,888,196; Issued Dec. 19, 1989 and Selden; European Patent 322,037; Published Jun. 28, 1989.

The nondigestible fat compositions of the present invention can also be used in or as shortening and oil products. The shortening and oil products can be used in frying applications such as preparation of french fried potatoes, potato chips from potato slices or fabricated potato slices, potato sticks, corn chips, tortilla chips, donuts, chicken, fish, and fried pies (e.g. turnovers). The shortening and oil products can also be used in preparing baked goods in any form, such as mixes, shelf-stable baked goods, and frozen baked goods, including, but not limited to, cakes, granola bars, brownies, muffins, bar cookies, wafers, biscuits, pastries, pies, pie crusts, and cookies, including sandwich cookies, chocolate chip cookies, and particularly storage stable dual-texture cookies as disclosed in Hong et al; U.S. Pat. No. 4,455,333; Issued Jun. 19, 1984. These baked goods can contain fruit, cream, or other fillings. Other baked goods uses include breads and rolls, crackers, pretzels, pancakes, waffles, ice cream cones and cups, yeast-raised bake goods, pizza and pizza crust, and baked farinaceous snack products and other baked salted snacks.

Other edible fat-containing products which may contain the nondigestible fat compositions of the present invention include ice cream, frozen desserts, cheese, cheese spreads, meats, meat analogs, chocolate confections, salad dressings, mayonnaise, margarine, spreads, sour cream, yogurt, coffee creamer, peanut butter, extruded snacks such as corn curls, corn puffs, pellet snacks, half products and other extruded snacks based on corn or other cereal grains such as wheat, rice and the like, roasted nuts and beverages such as milkshakes.

Edible fat-containing products which contain the nondigestible fat compositions of the present invention can include noncaloric or reduced calorie sweeteners alone or in combination with bulking agents. These noncaloric or reduced calorie sweeteners include, but are not limited to, aspartame, saccharin, alitame, thaumatin, dihydrochalcones, acesulfame, and cyclamates.

Bulking or bodying agents which can be useful in edible fat-containing products containing the nondigestible fat compositions herein include partially or wholly nondigestible carbohydrates, for example, polydextrose and cellulose or cellulose derivatives, such as D,L-sugars, carboxymethylcellulose, carboxyethylcellulose, hydroxypropylcellulose, methylcellulose, hydroxypropyl methylcellulose, and microcrystalline cellulose. Other suitable bulking agents include gums (hydrocolloids), starches, dextrins, fermented whey, tofu, maltodextrins, polyols, including sugar alcohols, e.g., sorbitol and mannitol, and carbohydrates, e.g., lactose.

The edible fat-containing products containing the nondigestible fat compositions herein can also include dietary fibers. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers can be used, such as psyllium and fibers from whole citrus peel, citrus albedo, sugar beets, citrus pulp and vesicle solids, apples, apricots, and watermelon rinds.

These dietary fibers can be in a crude or purified form. The dietary fiber used can be of a single type (e.g., cellulose), a composite dietary fiber (e.g., citrus albedo fiber containing cellulose and pectin), or some combination of fibers (e.g., cellulose and a gum). The fibers can be processed by methods known to the art.

The nondigestible fats of the present invention can be fortified with vitamins and minerals, particularly the fat soluble vitamins. The fat-soluble vitamins include A, vitamin D, and vitamin E and their precursors. (See Mattson; U.S. Pat. No. 4,034,083; Issued Jul. 5, 1977, herein incorporated by reference, which discloses fat-soluble vitamins useful in fortifying polyol fatty acid polyesters.)

Various other ingredients typically present in fat products can also be included in the nondigestible fat compositions of the present invention. These other ingredients include stabilizers to protect against oxidative deterioration at high temperatures. Silicone oils, particularly methyl and ethyl silicone oils, are useful for this purpose. Methyl silicones have also proven effective in reducing the rate of oil polymerization during frying. Other additives typically included in fat products such as minor amounts of optional flavorings, emulsifiers, anti-spattering agents, anti-sticking agents, antioxidants or the like can also be present.

F. Digestible Fat Compositions Containing the Solid Polyol Polyesters Herein

It has been found that the solid polyol polyesters of the claimed invention, in addition to being as passive oil loss control agents for liquid nondigestible oils, are also effective thickening agents for triglyceride oils. Accordingly, these solid polyol polyesters can be used as "thickening agents" or "hardstocks" by blending them in amounts of about 1% to about 40% (typically 1% to 15%, most typically 1% to 10%) with liquid digestible oils in the formulation of cooking and salad oils or semi-solid food products such as shortenings, as well as other food products which contain a combination of fat and non-fat ingredients, e.g., margarines, mayonnaise, frozen dairy desserts and the like. The oils for these compositions can be conventional digestible triglyceride oils such as cottonseed, corn, canola, or soybean, or medium or medium and long chain triglycerides.

G. Analytical Methods

A number of parameters used to characterize elements of the claimed invention are to be quantified by particular experimental analytical procedures. Each of these procedures is described in detail as follows:

1. Fatty Acid Composition of Polyol Polyesters

The fatty acid composition (FAC) of the polyol polyesters is determined by gas chromatography, using a Hewlett-Packard Model S712A gas chromatograph equipped with a flame ionization detector and a Hewlett-Packard Model 7671A automatic sampler.

The method is applicable to methyl esters of fatty acids having 8 to 24 carbon atoms and to animal fats, vegetable oils, marine oils and fatty acids after their conversion to methyl esters. The method permits quantitative separation of mixtures containing saturated and unsaturated methyl esters. The conditions specified in this method are not suitable for determining epoxy or oxidized fatty acids or fatty acids that have been polymerized.

Apparatus 1

1. The gas chromatograph, which is commercially available, should have as a minimum the following characteristics
   (a) Column oven, capable of heating the column to at least 220° C. and of maintaining the desired temperature to within ±1° C.
   (b) Sample inlet port with minimum dead space which is independently heated to a temperature 20°–50° C. higher than column temperature.
   (c) Detectors, thermal conductivity (TC) or flame ionization (FID), separately thermostated, which can be maintained at or above column temperature.
2. Recorder—If the recorder curve is to be used to calculate the composition of the mixture analyzed, an electronic recorder of high precision is required. The characteristics of the recorder should be
   (a) Rate of response below 1.0 seconds (the rate of response is the time taken for the recording pen to pass from 0 to 90 percent following the momentary introduction of a 100 percent signal).
   (b) Chart paper width, 25 cm (10 inches) minimum.
   (c) Chart paper speed, 25–100 cm/hr (10–40 inches/hour).
3. Integrator or Calculator (optional)—Rapid and accurate calculation can be performed with the help of an electronic integrator or calculator. This must give a linear response with adequate sensitivity, and baseline correction should be consistent with good chromatographic practice. Horizontal, non-horizontal and tangential baseline correction must be controlled by selectable electronic peak logic.
4. Syringe, maximum capacity 10 μL, graduated in 0.1 μL.
5. Chromatographic Column
   (a) The column must be constructed of a material inert to the substances to be analyzed, glass, or failing that, stainless steel (see Notes, 1), with a length of 1 to 3 m and an internal diameter of 2 to 4 mm.
   (b) Packing support, acid-washed and silanized diatomaceous earth, or other suitable inert support with a narrow range (25 μm) of grain size between the limits of 60–120 mesh (125–250 μm).
   (c) Stationary phase, polyester type of polar liquid (diethylene glycol polysuccinate, butanedial polysuccinate, ethylene glycol polyadipate), or any liquid (e.g., cyanosilicones), meeting the requirements below. The stationary phase should amount to 5–20 percent of the packing. A nonpolar stationary phase, such as methyl silicone, fluid or gum, can be used for separations of fully saturated materials.

Reagents

1. Gases
   (a) Carrier gas for TC detector, helium, minimum purity 99.95 mol %; for FID, helium, nitrogen, or argon, minimum purity 99.95 mol %.
   (b) FID, hydrogen, minimum purity 99.95 mol %; air, dry (dew point −75F maximum) and hydrocarbon free (less than 2 ppm hydrocarbons equivalent $CH_4$).
2. References Standards—A mixture of methyl esters, or the methyl esters of an oil of known composition, preferably similar to that of the fatty matter to be analyzed. Reference mixtures simulating most fats and oils may be obtained from Applied Science Laboratories, Inc., PO Box 440, State College, Pa. 16801. Supelco, Inc., Supelco Park, Bellefonte, Pa. 16823. Nu Chek Prep, Inc., PO Box 172, Elysian, Minn. 56028. Analabs, Inc., 80 Republic Drive, North Haven, Conn. 06473. Alltech Associates, Inc., 2501 Waukegan Road., Deerfield, Ill. 60015.

Preparation of Methyl Esters

AOCS Official Method Ce 2-66 is recommended

Procedure

1. Conditioning a new column while disconnected from detector by holding it about 10° C. above its operating temperature with flow of inert gas at 20–60 mL/min for approximately 16 hours and then an additional 2 hours at 20° C. above its operating temperature. In no case exceed the manufacturer's recommended maximum temperature.
2. Determining optimal operating conditions
   (a) In selecting the test conditions, the following variables must be taken into account: length and diameter of the column, temperature of the column, carrier gas flow, resolution required, size of the sample for analysis and time of analysis. The size of the sample should be chosen so that the assembly of detector and electrometer gives a linear response. As a rule, the following figures will lead to the desired results, viz., at least 2,000 theoretical plates for methyl stearate and its elution within about 15 minutes:

| Internal Diameter of Column | Carrier Gas Supply |
|---|---|
| 2 mm | 15–25 ml/min |
| 3 mm | 20–40 ml/min |
| 4 mm | 40–60 ml/min |

| Concentration of Stationary Phase | Temperature |
|---|---|
| 5 percent | 175° C. |
| 10 percent | 180° C. |

| | |
|---|---|
| 15 percent | 185° C. |
| 20 percent | 185° C. |

(b) Where the apparatus allows, the injection port should be at a temperature of about 250°–275° C. and the detector at a temperature equal to, or higher than, that of the column.

(c) The flow of hydrogen to the flame ionization detector is, as a rule, about 0.5 to 1 times that of the carrier gas, and the flow of air about 5 to 10 times that of the hydrogen.

3. Determining the efficiency and the resolution (a) Carry out the analysis of a mixture of methyl stearate and oleate in about equivalent proportions (e.g., methyl esters from cocoa butter). Choose the size of the sample, the temperature of the column and the carrier gas flow so that the maximum of the methyl stearate peak is recorded about 15 minutes after the solvent peak and rises to three-quarters of the full scale. Calculate the number of theoretical plates n (efficiency) by the formula $$n = 16(dR_1/w_1)^2$$

and the resolution, R, by the formula $$R = 2\Delta/(w_1 + w_2)$$

where $dR_1$ is the retention distance, measured in mm, from the start to the maximum peak of methyl stearate.

$w_1$ and $w_2$ are the widths, in mm, of the peaks for methyl stearate and methyl oleate, measured between the points of intersection of the tangents at the inflection points of the curve with the base-line.

$\Delta$ is the distance between the respective peak maxima for methyl stearate and oleate.

(b) Operating conditions to be selected are those which will afford at least 2,000 theoretical plates for methyl stearate, and a resolution at least 1.25. Additionally, linolenic acid ($C_{18:3}$) ester should be separable from archidic acid ($C_{20:0}$) and gadoleic acid ($C_{20:1}$) esters.

(c) As a rule, the operating conditions will be those defined above. Nevertheless, it is possible to work with a lower column temperature where the determination of acids below $C_{12}$ is required or at a higher temperature when determining fatty acids above $C_{20}$.

(d) On occasion, it is possible to employ temperature programming in both the previous cases. For example, if the sample contains the methyl esters of fatty acids below $C_{12}$, inject the sample at 100° C. column temperature and immediately raise the temperature at a rate of 4°–8° C./minute to the optimum. In some cases, the two procedures can be combined. After the programmed heating, continue the elution at a constant temperature until all the components have been eluted. If the instrument does not employ programmed heating, work at two fixed temperatures between 100° C. and 195° C. Liquid phase characteristics will determine the starting temperature or the upper temperature if the analysis is performed iso-thermally.

4. Analysis (a) The sample for examination should be 0.1–2 μL of the solution of methyl esters obtained according to AOCS Official Method Ce 2-66. In the case of esters not in solution, prepare an approximate 1–10% solution and inject 0.1–1 μL of this solution.

(b) If the object is to determine constituents present only in trace amounts, the sample size may be increased (up to tenfold).

Calculations

1. Identification of Peaks (a) Analyze the reference standard mixture of known composition under the same operating conditions as those employed for the sample, and measure the retention distances (or retention times) for the constituent esters. Construct graphs showing the logarithm of the retention distance (or retention time) as a function of the number of carbon atoms of the acids; under isothermal conditions, the graphs for straight chain esters of the same degree of unsaturation should be straight lines. These straight lines are approximately parallel.

(b) Identify the peaks for the sample from these graphs, by interpolation if necessary.

(c) It is necessary to avoid conditions which permit masked peaks, i.e., where the resolution is not adequate to separate two components.

2. Quantitative Analysis (a) Apart from exceptional cases, assume that the whole of the components of the sample are represented on the chromatogram, so that the total of the areas under the peaks represents 100% of the consistuents (total elution).

(b) If the equipment includes an integrator, use the figures obtained therefrom. If not, determine the area under each peak by multiplying the height by the breadth at mid-height and, where necessary, take into account the various attenuations used during the recording.

(c) For the general case, in which significant amounts of components below $C_{12}$ are absent, calculate the content of a particular constituent (expressed as percent of methyl esters) by determining the percentage represented by the area of the corresponding peak relative to the sum of the areas of all the peaks.

Area percent of the component i expressed as methyl ester=

$$\frac{A_i}{\Sigma A_i} \times 100$$

Where $A_i$ = area of the peak corresponding to component i.

$\Sigma A_i$ = sum of the areas under all the peaks.

(d) Correction factors, particularly in the presence of acids below $C_{12}$, of acids with secondary groups, or when using a TC detector, must be used to convert the percentages of peak areas into mass-percentages of the components. Determine the correction factors with the help of a chromatogram derived from the analysis of a reference mixture of methyl esters of known composition under operating conditions identical with those used for the sample.

For this reference mixture:

Weight percent (m/m) of component i=

$$\frac{B_i}{\Sigma B_i} \times 100$$

Where $B_i$ = mass of component i in the reference mixture $\Sigma B_i$=total of the masses of the various components of the reference mixture From the chromatogram of the reference mixture, one can calculate:

$$\text{Area percent of component } i = \frac{C_i}{\Sigma C_i} \times 100$$

Where $C_i$=area under the peak corresponding to component i $\Sigma C_i$=sum of the area under all the peaks.

Whence $$\text{Correction factor } K_i = \frac{B_i \times \Sigma C_i}{C_i \times \Sigma B_i}$$

Commonly, the correlation factors are made relative to $K_{C_{16}}$ so the relative factors become:

$$K'_i = \frac{K_i}{K_{C_{16}}}$$

Then the content of each component in the sample is given by:

Weight percent (m/m) of component i, expressed as methyl esters=

$$\frac{(K'_i \times A_i)}{\Sigma(K'_i \times A_i)} \times 100$$

(e) Use an internal standard, notably in determinations when all of the fatty acids are not eluted. The internal standard may be the methyl ester of the $C_{13}$ fatty acid. The correction factor for the internal standard should be determined:

Weight percent (m/m) of component i, expressed as methyl esters=

$$\frac{m_{C_{13}} \times K'_i \times A_i}{m \times K'_{C_{13}} \times A_{C_{13}}} \times 100$$

Where $m_{C_{13}}$=mass, in mg, of the internal standard added to sample m=mass, in mg, of the sample

*$K'_{C_{13}}$=correction factor for the internal standard relative to $K_{C_{16}}$ $A_{C_{13}}$=area of the peak corresponding to the internal standard $A_i$=area of the peak corresponding to component i $K'_i$=correction factor of component i relative to $K_{C_{16}}$ $$*K'_{C_{13}} = \frac{K_{C_{13}}}{K_{C_{16}}}$$

*Determined be adding a known amount $C_{13}$ methyl ester to the reference mixture and then following the above procedure for determining $K'_i$.

(f) Expression of the results

Give the results to: 3 significant figures for contents over 10%, 2 significant figures for contents between 1 and 10 percent, 1 significant figure for contents below 1 percent, i.e., with one figure beyond the decimal point in every case.

Precision

1. Repeatability—The difference between the results of two determinations carried out on the same day by the same operator using the same apparatus for the same esters and for constituents present in excess of 5% should not exceed a relative figure of 3% of the determined value, with an absolute value of 1%. For components present in amounts of less than 5%, the repeatability in relative terms diminishes progressively as the content is reduced.

2. Reproducibility—The difference between the results obtained in two different laboratories for constituents present in excess of 5% should not exceed a relative figure of 10% of the determined value, with an absolute maximum of 3%. For constituents present in amounts less than 5%, the reproducibility in relative terms diminishes progressively as the content is reduced.

Notes

1. If polyunsaturated components with more than three double bonds are present, they may decompose in a stainless-steel column.

2. It is recommended that chromatographers read "Standard Recommended Practice for General Gas Chromatography Procedures", ASTM Designation E260-73; "Standard Recommended Practice for Gas Chromatography Terms and Relationships", ASTM Designation E355-77; and "Standard Recommended Practice for Testing Flame Ionization Detectors Used in Gas Chromatography", ASTM Designation E594-77.

2. Ester Distribution of Sucrose Polyesters

The relative distribution of the individual octa-, hepta-, hexa- and penta- esters, as well as collectively the tetra- through mono- esters, of the sucrose polyesters can be determined using normal-phase high performance liquid chromatography (HPLC). A silica gel-packed column is used in this method to separate the polyester sample into the respective ester groupings noted above. Hexane and methyl-t-butyl ether are used as the mobile phase solvents. The ester groupings are quantitated using a mass detector (i.e. an evaporative light-scattering detector). The detector response is measured and then normalized to 100%. The individual ester groups are expressed as a relative percentage.

3. Slope of Solid Fat Content (SFC) Profile of Nondigestible Fat Measured in °F.

Before determining the SFC values, a sample of the nondigestible fat is heated to a temperature of 140° F. (60° C.) or higher for at least 30 minutes or until the sample is completely melted. The melted sample is then tempered as follows: at 80° F. (26.7° C.) for 15 minutes; at 32° F. (0° C.) for 15 minutes; at 80° F. (26.7° C.) for 30 minutes; at 32° F. (0° C.) for 15 minutes. After tempering, the SFC values of the sample at temperatures of 50° F. (10° C.), 70° F. (21.1° C.), 80° F. (26.7° C.), 92° F. (33.3° C.), and 98.6° F. (37° C.) are determined by pulsed nuclear magnetic resonance (PNMR) after equilibration for 30 minutes at each temperature. The slope of the SFC profile is calculated by subtracting the SFC value at 70° F. (21.1° C.) from the SFC value at 98.6° F. (37° C.) and then dividing by 28.6. The method for determining SFC values by PNMR is as follows:

Apparatus

1. Praxis Pulsed NMR SFC 900 Solid Fat Analyzer available from The Praxia Corporation, San Antonio, Tex., 78251, or equivalent.

2. Sample tubes. Test tubes, culture, disposable, Pyrex or Kimax glass, 10 mm OD× 75 mm length without rims, with dimensions 0.380+0.005 inches OD (9.65±0.13 mm OD).

3. Oven maintained at 70° C.±2° C.

4. Corks, size 0.
5. Tissues for wiping sample tubes.

Reagents

Olive oil reference liquids having the following compositional analysis (see Notes, 2)

|  | Spanish | Italian |
|---|---|---|
| Iodine Value: | 84–87 | 85–88 |
| Saponification Value: | 189–195 | 192–195 |
| Fatty Acid Composition |  |  |
| $C_{16}$ | $9.5 \pm 1.0$ | $14.0 \pm 1.5$ |
| $C_{18}$ | $3.5 \pm 0.5$ | $2.5 \pm 0.5$ |
| $C_{18:1}$ | $76 \pm 2.0$ | $65.0 \pm 3.0$ |
| $C_{18:2}$ | $7.0 \pm 1.5$ | $14.0 \pm 1.5$ |
| $C_{18:3}$ | $1.0 \pm 0.2$ | $1.0 \pm 0.2$ |

Procedure

1. Filling the sample tubes
   (a) Heat the sample in the 70° C. oven until liquid and mix well.
   (b) Fill the sample tube with the melted sample to approximately 15 mm from the top.
   (c) Place cork in top of sample tube.
   (d) Wipe sample tube with tissue making sure outside of tubes are clean.
2. Tempering of the sample and pulsed nmr measurements
   (a) Insert sample tubes containing all samples to be measured and the reference olive oil sample into the sample tempering ports of the 60° C. probe.
   (b) Equilibrate all samples and reference oil for 30 minutes.
   (c) Set the instrument conditions as follows

| Auto/Manual Switch | Auto |
|---|---|
| Probe/Selector | 6 |
| FID/Temp Switch | FID |
| Response | Fast |
| Variable Delay | 100 × 1 |
| Clock | 2 × 1.0 |
| Function | 90° C. |
| Program Counter | 8 |
| Gain and Instrument | Refer to Operators |
| Background | Manual |
| Probe Temperatures | Refer to Operators Manual |

(d) Insert the olive oil reference sample into the analysis port and measure the NMR reading (see Notes, 3).
   (e) Insert each sample into the analysis port and measure the NMR reading of each sample.
   (f) Transfer the reference oil and samples to the 26.7° C. probe and equilibrate for exactly 15 minutes.
   (g) Transfer the reference oil and samples to the 0° C. probe and equilibrate for exactly 15 minutes.
   (h) Transfer the reference oil and samples to the 26.7° C. probe and temper for exactly 30 minutes.
   (i) Transfer the reference oil and samples to the 0° C. probe and chill for exactly 15 minutes.
   (j) Transfer the reference oil and samples to the 10° C. probe and equilibrate for exactly 30 minutes.
   (k) Set clock to 1×1.0 an Probe Selector to 1.
   (l) Measure the NMR reading of the reference oil and samples.
   (m) Transfer the reference oil and samples to the 21.1° C. probe and equilibrate for exactly 30 minutes.
   (n) Set Probe Selector to 2.
   (o) Measure the NMR reading of the reference oil and the samples.
   (p) Transfer the reference oil and samples to the 26.7° C. probe and equilibrate for exactly 30 minutes.
   (q) Set Probe Selector to 3.
   (r) Measure the NMR reading of the reference oil and the samples.
   (s) Transfer the reference oil and samples to the 33.3° C. (or to 40.6° C.) probe and equilibrate for exactly 30 minutes.
   (t) Set Probe Selector to 4.
   (u) Measure the NMR reading of the reference oil and samples.
   (v) Transfer the reference oil and samples to the 37.8° C. (or to 40.6° C.) probe and equilibrate for exactly 30 minutes.
   (w) Set Probe Selector to 5.
   (x) Measure the NMR reading of the reference oil and samples.

Calculations:
1. Solid Fat Content (*SFC*) at temperature *TC* =

$$\frac{\text{Reference oil at 60° C.}}{\text{Sample at 60° C.}} \times \frac{\text{Sample at } TC}{\text{Reference Oil } TC} \times 100$$

Example:
NMR Readings:

| Reference Oil at 60° C. | 105.6 |
|---|---|
| Sample at 60° C. | 105.4 |
| Reference Oil at $T$ °C. (10.0) | 98.8 |
| Sample at $T$ °C. (10.0) | 80.2 |

$$\% \text{ Solid Fat} = 100 - \frac{105.6}{105.4} \times \frac{80.2}{98.8} \times 100 = 18.67\%$$

Precision

Data from the AOCS collaborative study which validated this method show the following reproducibility can be expected 1.

1. Within and between laboratories, separate determinations of margarine-type oils should be plus or minus one standard deviation for temperatures listed:

|  | 10.0° C. | 21.1° C. | 26.7° C. | 33.3° C. | 37.8° C. |
|---|---|---|---|---|---|
| Std. dev. | 0.6 | 0.5 | 0.6 | 0.6 | 0.4 |

2. Within and between laboratories, separate determinations of plasticized shortening-type oils should be plus or minus one standard deviation for temperatures listed:

|  | 10.0° C. | 21.1° C. | 26.7° C. | 33.3° C. | 37.8° C. |
|---|---|---|---|---|---|
| Std. dev. | 0.7 | 0.7 | 0.6 | 0.5 | 0.4 |

3. Within and between laboratories, separate determination of non-cocoa butter-type confectionery fats should be plus or minus one standard deviation for temperatures listed:

|  | 10.0° C. | 21.1° C. | 26.7° C. | 33.3° C. | 37.8° C. |
|---|---|---|---|---|---|
| Std. dev. | 0.6 | 1.0 | 1.1 | 0.5 | 0.4 |

4. Within and between laboratories, separate determinations for unhydrogenated palm-type oils should be plus or minus one standard deviation for temperatures listed (see Notes, 4):

|  | 10.0° C. | 21.1° C. | 26.7° C. | 33.3° C. | 37.8° C. |
|---|---|---|---|---|---|
| Std. dev. | 1.0 | 0.8 | 0.6 | 0.5 | 0.4 |

5. Within and between laboratories, separate determinations tristearin in olive standards should be plus or minus one standard deviations at 10° C. for the percent tristearin in olive oils listed (see Notes, 5):

|  | 10.0° C. | 21.1° C. | 26.7° C. | 33.3° C. | 37.8° C. |
|---|---|---|---|---|---|
| Std. dev. | 0.2 | 0.2 | 0.4 | 0.2 | 0.1 |

Notes
1. The basic procedure described is applicable at temperatures and times other than those specified and the Committee recognizes that sometimes such deviations are necessary. In 1989, a collaborative study effort by the AOCS NMR Technical Committee was begun to establish harmonized tempering conditions for existing NMR instruments and for other types of fats and oils. The Committee expects this study to be completed in 1991.
2. The basic procedure described is dependent upon the chemical stability of the olive oil reference sample. Excessive heating or abuse can cause oxidation resulting in the formulation of solids and lower pulsed NMR readings. The Committee recommends replacement of the reference sample oil every three months with fresh olive oil which has been kept under refrigeration. While it is not the Committee's place or intent to recommend a specific oil, it is noted that the collaborative study was conducted using a high grade Lucca Olive Oil from Italy.
3. Push retest button one time before making NMR reading on first sample tested in each probe, as recommended by the Instrument Manufacturer.
4. The basic procedure described is applicable to unhydrogenated palm oils and blends containing unhydrogenated palm oils. The Committee recognized that other palm oil type samples and/or blends do produce poor reproducibility and further work is planned in this direction to establish tempering conditions prior to measurement.
5. These values of reproducibility are an indication of the precision obtainable by this method of measurement when polymorphic stability of the sample is not a factor. The tristearin in olive oil mixtures are also used as reference samples for the calibration of the instrument. These mixtures are melted and liquid readings taken at 70° C. before being tempered and measured by this method. The Solid Fat Content (SFC) values measured agree well with the percentage of solids by weight. A single fifth order polynomial regression equation is recommended for solids contents of 95% or less. Polynomial coefficients, correlation coefficients and interpolation tables for conversion of calculated solids to calibration corrected solids can be obtained from the manufacturer for each instrument. The calibration procedure is also provided by the manufacturer.

4. Complete Melting Point of Polyol Polyesters by Differential Scanning Calorimetry (DSC)

The complete melting point of the polyol polyester material or polyol polyester-containing particles used in this invention can be determined by DSC as follows:

Equipment
Perkin-Elmer 7 Series Thermal Analysis System, Model DSC7, manufactured by Perkin-Elmer, Norwalk, Conn.
Procedure
1. Sample of polyol polyester material or polyol polyester-containing blend is heated to at least 10° C. above the temperature at which all visible solids are melted and mixed thoroughly.
2. 10±2 mg of sample is weighed into sample pan.
3. A scan is performed from about 10° C. above the temperature at which all visible solids are melted to −60° C. at 5° C. per minute.
4. The temperature of the sample is maintained at −60° C. for 3 minutes and scanned from −60° C. to the original starting temperature at 5° C. per minute (i.e., from about 10° C. above the temperature at which all visible solids are melted).
5. The complete melt point is the temperature at the intersection of the base line (i.e. specific heat line) with the line tangent to the trailing edge of the last (e.g., highest temperature) endothermic peak.

5. Acid Value of the Solid Polyol Polyester

The solid polyol polyester can be titrated with standardized KOH to a phenolphthalein endpoint. The procedure is described in *Official Methods and Recommended practices of the American Oil Chemists Society*, 4th Ed., 1989, Procedure 3a-63. A blank (no sample added) is titrated also.

The Acid Value can then be calculated according to the following equation:

$$AV = ((A-B) \times N \times 56.1)/W$$

where

A = volume in mls of KOH required to titrate the sample
B = volume in mls of KOH required to titrate the blank
N = normality of KOH
W = sample weight in grams 6. Hydroxyl Value of Solid Polyol Polyester The free hydroxyl groups of the sample can be quantitatively acetylated with acetic anhydride in pyridine. After acetylation, residual acetic anhydride is hydrolyzed with excess water and the acetic acid remaining is titrated with standardized ethanolic KOH to a phenolphthalein endpoint. A blank (no sample added) is run through the procedure and titrated also. The procedure is described in *Official Methods and Recommended Practices of the American Oil Chemists Society*, 4th Ed., 1989, Procedure Cd 13-60.

The Hydroxyl Value is then calculated according to the following equation:

$$HV = (((B-S) \times N \times 56.1)/W) + AV$$

where

B = volume in mls of KOH required to titrate the blank
S = volume in mls of KOH required to titrate the sample
N = normality of the KOH
AV = acid value of the sample (described herein above)

7. Thickness of Solid Polyol Polyester Particle (Light Microscopy)

The thickness of the solid polyol polyester particles formed in the nondigestible fat compositions herein may be estimated at room temperature with a Nikon Microphot video-enhanced light microscope (VELM) using Hoffman Modulation Contrast (HMC) optics according to the following method:

1. A small portion (i.e., 1–10 mg) of the nondigestible fat sample with the solid polyol polyester particles dispersed therein is placed on a microscope slide and covered. The slide is placed under the microscope.
2. The sample is examined using an HMC 100X oil objective as the standard lens in conjunction with a 10× eyepiece lens.
3. A microscope-mounted video camera and associated controller are used for video enhancement to facilitate differentiation between the sample and the background.
4. The thickness of the solid polyol polyester particles is measured in um.

This method permits differentiation of particles having thicknesses just within the resolution of the VELM (approximately 0.2–0.5 um). Particle thickness of particles having smaller dimensions can be determined by the Freeze Fracture Method described hereinafter.

(Note: No special sample preparation is required, other than obtaining a representative sample. The samples should be melted and cooled ambiently.)

Reference: Robert Hoffman, "The Modulation Contrast Microscope: Principles and Performances", *Journal of Microscopy*, Vol. 10, Pt 3, August 1977, pp. 205–222.

8. Thickness of Solid Polyol Polyester Particles-Freeze Fracture Transmission Electron Microscopy The three-dimensional topography of particles of polyol polyesters and their size can be determined by a freeze-fracture transmission electron microscopy (ff-tem) method.

This freeze-fracture method is carried out as follows:

1. The outside cavity of a freezing container is filled with liquid $N_2$ and the inner dewar of the freezing container is filled with liquid ethane (normal melting temperature of −172° C.). The ethane is allowed to freeze.
2. A small amount (1–2 ul) of the nondigestible fat sample with the solid polyol polyester particles dispersed therein is placed in the well of a gold-plated Balzers specimen holder. (Note: for very fluid samples, 1–2 ul of sample is placed on a gold planchet (Baizers) and another planchet is placed on top of the first to form a sandwich.)
3. Most of the frozen ethane in the dewar is melted by inserting a metal heat sink (e.g., tweezers) into the dewar.
4. Immediately after melting the ethane, the specimen holder containing the nondigestible fat sample is picked up using a pair of tweezers and rapidly plunged into the liquid ethane.
5. After a few seconds, the specimen holder is removed from the ethane, quickly touched to the tip of a camel's hair brush to remove excess ethane, and immediately immersed in the liquid $N_2$ to keep the sample cold.
6. The sample is transferred under liquid $N_2$ to a JEOL JFD-9000C sample holder and then transferred into the chamber of a JEOL JFD-9000C freeze-fracture unit. The temperature of the unit should be about −175° C. Vacuum should be at least $8 \times 10^{-7}$ torr.
7. A knife is cooled to a temperature of about −165° C.
8. The sample is fractured in the JEOL chamber using the pre-cooled knife.
9. Platinum-carbon is deposited onto the fractured sample at a 45° angle for 4.5 seconds, followed by carbon deposition at a 90° angle for 25 seconds to form a replica of the fractured sample. The high voltage is 2500 V and the current is 70 mA.
10. The samples are removed from the freeze fracture unit and cleaned using 3 washes of chloroform.
11. The replica is picked up on a 300 mesh copper EM grid and examined in a transmission electron microscope.
12. Images are recorded on negative film and positive prints are made from the negatives.
13. The thickness of the polyol polyester particles is measured in nm.

References:

Rash, J. E. and Hudson, C. S., *Freeze Fracture: Methods, Artifacts, and Interpretations*, New Haven Press, New York, 1979.

Stolinski and Breathnach, *Freeze Fracture Replication of Biological Tissues*, Academic Press, London, 1975.

Steinbrecht and Zierold, *Cryotechniques in Biological Electron Microscopy*, Springer-Verlag, Berlin, 1987.

H. Specific Examples

Preparation of the solid polyol polyesters and the fat compositions of the present invention is illustrated by the following examples:

EXAMPLE I

Solid Sucrose Polyester Preparation

Ricinoleic Methyl Ester Preparation

Ricinoleic methyl esters are made from castor oil by methanolysis, using sodium methoxide as a catalyst. About 420 grams of castor oil are added to a 3-liter glass reactor along with about 84 grams of methanol, and about 5.9 grams of sodium methoxide solution (about 25% sodium methoxide in methanol). The mixture is agitated and heated at atmospheric pressure and about 65° C. for about 1.25 hours. The methanol refluxes back to the reactor in a reflux condenser. About 50 grams of water are added to the reactor, the mixture is agitated, then the agitation is turned off, and the mixture is allowed to settle. The water, glycerin and unreacted methanol settle to the bottom of the reactor in a single phase, and this layer is drawn off. This methanolysis and water washing procedure is repeated two more times, and the methyl esters are then flash distilled. About a 2% top cut of glycerin, water and other lighter boiling materials are taken off by vacuum distillation, then the bulk of the methyl esters are flash distilled over in a middle cut, leaving about a 10% residual bottom cut in the distillation flask. The middle cut contains about 87% by weight ricinoleic methyl esters. This middle cut is the product to be used in the sucrose polyester transesterification.

Behenic Methyl Ester Preparation

Behenic methyl esters are made from hydrogenated high erucic acid rapeseed oil. About 870 grams of hydrogenated high erucic acid rapeseed oil, about 174 grams of methanol, and about 12.2 grams of sodium methoxide solution (25% in methanol) are added to a spherical 3-liter glass reactor. The reactor has a heating mantle, thermometer, temperature controller, reflux condenser, variable speed agitator, vacuum take-off, and bottom outlet. The mixture is reacted at about 65° C. for approximately 1.5 hours, while refluxing the methanol. The agitation is stopped, and the glycerin is allowed to settle for about 30 minutes. The glycerin settles to the bottom of the reactor, and is removed through the bottom outlet. About 30 additional grams of methanol, and about 5.2 grams of sodium methoxide solution (25% in methanol) are added to the glass reactor, and the mixture is reacted at about 65° C. for about 30 minutes. The agitation is stopped, the glycerin is settled for about 30 minutes, and removed through the bottom outlet. About 100 grams of water are added to the mixture, stirred, allowed to settle, and removed through the bottom outlet. The water-washing procedure is repeated two more times. The reflux condenser is removed, and vacuum is broken, and a fractionation column is added to the reactor. The reactor is heated to about 170°–200° C. under a vacuum of about 0.3–1.0 mm Hg. Approximately 50% of the first material to evaporate from the column is collected and discarded. The next 40% (approximately) of the material to evaporate from the column is collected as product. This product is approximately 92% by weight methyl behenate.

Sucrose Esterification

The reaction apparatus used to prepare the sucrose polyester in this example is a one liter glass reaction flask fitted with a constant speed agitator, thermometer, McLeod gauge, and vacuum take-off. A heating mantle surrounds the reactor, and the temperature in the reactor is maintained by a Thermowatch. Vacuum is drawn on the reactor by a vacuum pump, and a dry ice trap is placed between the reactor vacuum take-off and the vacuum pump to condense and collect the methanol byproduct from the reaction.

About 46.2 grams of the ricinoleic methyl esters are mixed with about 367.5 grams of behenic methyl esters. The molar ratio of castor methyl esters to hydrogenated and distilled rapeseed methyl esters is about 1:7. About 172.3 grams of the methyl ester mixture is added to the one liter reactor along with about 34.4 grams of powdered sucrose, about 24 grams of potassium stearate and about 1.4 grams of powdered potassium carbonate. The reactants are heated at about 135° C. at about 15 mm Hg absolute for about 1.5 hours. At this point the remaining methyl esters (about 241.4 grams) and about 1.4 grams of potassium carbonate are added to the reactor. The reactants are heated to about 135° C. at about 1–2 mm Hg absolute for about 5 hours.

The reaction mixture is cooled under nitrogen to about 75° C., and about 30 grams of water are added and mixed in. The mixture is centrifuged (Fischer Scientific Model Marathon 10K Centrifuge) at about 2500 RPM for about 2 minutes, then the supernatant product is decanted from the soap and water layer. About 3.8 grams of silica are added to the product, and the mixture is filtered to remove the last traces of soap and silica.

The excess methyl esters are evaporated from the sucrose polyester product by feeding the material through a 2 inch Pope wiped film evaporator. The wall temperature is about 235° C., and the vacuum is maintained at about 0.05 mm Hg absolute. The sucrose polyester product from the bottom of the evaporator is the finished product. This solid sucrose polyester product is an improved oil thickening agent, that can be used for passive oil loss control when blended with liquid sucrose polyesters.

Fat Composition Preparation

About 1–10% by weight of this solid sucrose polyester product can be added to a liquid sucrose polyester in which the sucrose is substantially completely esterified with the fatty acid groups of cottonseed oil. The blend is heated to a temperature higher than the melting point of the solid sucrose polyester, and then cooled back to room temperature at a rate of 33.3° F./min. The cooling brings about crystallization of the solid sucrose polyester material in the form of small, platelet-like particles which are dispersed in the liquid sucrose polyester. FIG. 1 is a photomicrograph depicting the two-dimensional platelet-like structure of the solid sucrose polyester particles. These particles have a thickness of less than about 25 nm as measured by Freeze Fracture Transmission.

The nondigestible fat composition of this Example I comprising solid particles of sucrose polyester dispersed in the liquid sucrose polyester has an SFC profile slope of −0.1% solids/°F. as determined by the method described hereinbefore in the Analytical Methods section. This Example I composition is suitable for use as a food fat, and does not present the passive oil loss problem which would otherwise result if only the liquid sucrose polyester were to be used as a food fat. Also, as a result of the low solids levels used to prepare the Example I fat composition, food products made from this fat composition are not unacceptably waxy tasting.

The liquid sucrose polyester used in this Example I has the attributes set forth hereinafter in Table I.

TABLE I

|  | Liquid Sucrose Polyester % |
|---|---|
| FATTY ACID CONTENT |  |
| $C_{12}$ | — |
| $C_{14}$ | 0.3 |
| $C_{16}$ | 20.3 |
| $C_{17}$ | 0.1 |
| $C_{18}$ | 6.2 |
| $C_{18:1}$ | 37.3 |
| $C_{18:2}$ | 34.2 |
| $C_{18:3}$ | 0.3 |
| $C_{20}$ | 0.3 |
| $C_{22}$ | — |
| $C_{24}$ | — |
| Other | 0.5 |
| ESTER DISTRIBUTION |  |
| Octa | 74.6 |
| Hepta | 25.0 |
| Hexa | <0.1 |
| Lower | <0.1 |

EXAMPLE II

Solid Sucrose Polyester Preparation

About 46.2 grams of castor methyl esters are mixed with about 367.5 grams of hydrogenated and distilled rapeseed methyl esters. The molar ratio of castor methyl esters to hydrogenated and distilled rapeseed methyl esters is about 1/7. About 172.3 grams of this methyl ester mixture are added to a 1-liter spherical glass reactor along with about 34.4 grams of powdered sucrose, about 24 grams of powdered potassium stearate and about 1.4 grams of powdered potassium carbonate. The reactor has a heating mantle, thermometer, temperature controller, variable speed agitator, vacuum take-off, and bottom outlet. The mixture is agitated and heated at about 135° C. at about 15 mm Hg for about 1.5 hours. After about 1.5 hours, the vacuum is broken with nitrogen, and the remaining 241.4 grams (approximately) of the methyl ester mixture, along with about 1.4 grams of potassium carbonate are added to the reaction mixture. This mixture is reacted at about 135° C. under about 0.7–4.8 mm Hg vacuum for about 5 hours. The mixture is cooled to about 75° C., and about 30 grams of water are added to the mixture. The mixture is transferred to jars and centrifuged (Fischer Scientific Model marathon 10K Centrifuge) at about 2500 RPM for about 2 minutes. The liquid in the jars is then decanted from the soap layer at the bottom of the jars.

About 5 grams of silica are added to the decanted liquid, and the mixture is stirred for about 30 minutes at about 75° C. The mixture is then filtered through filter paper using a Buchner funnel. The filtrate is then fed through a Pope 2-inch diameter wiped film evaporator at approximately 30 grams/hour to distill the unreacted methyl esters. The evaporator operates at about 235° C. under about 0.05–0.07 mm Hg. The product is then collected from the evaporator and cooled to ambient temperature.

The solid sucrose polyester product has an Acid Value of 0.1 and a Hydroxyl Value of 33.2.

The 12-hydroxy groups of the ricinoleic acids bound to sucrose are themselves esterified with fatty acids during the reaction. This is verified by use of a multinuclear NMR experiment called INAPT (Insensitive Nuclei Assigned by Polarization Transfer). The procedure is described in Johnson, L. *Relaxation Times.*, 7(1):4 (1990). The experiment detects long-range heteronuclear coupling, $^3J_{CH}$. In this case the C-12 methine $^1H$ resonance of the ricinoleic acyl group in the proton spectrum (chemical shift of 4.9 ppm relative to TMS) is coupled to one carbonyl $^{13}C$ resonance in the carbon spectrum (chemical shift of 173.2 ppm relative to TMS). This unique carbonyl resonance is not present in spectra of mixtures of sucrose hexa-, hepta-, and octabehenate. It comes from the carbonyl of the fatty acyl radicals esterified to the $C_{12}$ hydroxyl group of the ricinoleic acyl radical.

Fat Composition Preparation

About 1–10% by weight of this solid sucrose polyester product can be added to the liquid sucrose polyester described hereinbefore in Example I. The blend is heated to a temperature higher than the melting point of the solid sucrose polyester, and then cooled back to room temperature at a rate of 33.3° F./min. The cooling brings about crystallization of the solid polyol polyester material in the form of small, platelet-like particles which are dispersed in the liquid sucrose polyester.

The nondigestible fat composition of this Example II comprising solid particles of sucrose polyester dispersed in the liquid sucrose polyester has an SFC profile slope of −0.1 as determined by the method described hereinbefore in the Analytical Methods section. This Example II composition is suitable for use as a food fat, and does not present the passive oil loss problem which would otherwise result if only the liquid sucrose polyester were to be used as a food fat. Also, as a result of the low solids levels used to prepare the Example II fat composition, food products made from this fat composition are not unacceptably waxy tasting.

EXAMPLE III

Solid Sucrose Polyester Preparation

This Example III uses the same apparatus and the procedure as the previous Examples. About 61.8 grams of castor methyl esters are mixed with about 304.4 grams of hydrogenated-and-distilled rapeseed methyl esters. The molar ratio of caster methyl esters to hydrogenated and distilled rapeseed methyl esters is about 1.5/6.5. About 142.5 grams of this methyl ester mixture are added to a 1-liter spherical glass reactor along with about 34.4 grams of powdered sucrose, about 24 grams of powdered potassium stearate and about 1.4 grams of powdered potassium carbonate. The mixture is agitated and heated at about 135° C. at about 15 mm Hg vacuum for about 1.5 hours. After about 1.5 hours, the vacuum is broken with nitrogen, and the remaining 223.7 grams (approximately) of the methyl ester mixture, along with about 1.4 grams of potassium carbonate are added to the reaction mixture. This mixture is reacted at about 135° C. under about 0.5–5.8 mm Hg vacuum for about 5 hours. The mixture is cooled to about 75° C., and about 30 grams of water are added to the mixture. The mixture is transferred to jars and centrifuged (Fischer Scientific Model Marathon 10K Centrifuge) at about 2500 RPM for about 2 minutes. The liquid in the jars is then decanted from the soap layer at the bottom of the jars. About 5 grams of silica are added to the decanted liquid, and the mixture is stirred for about 30 minutes at about 75° C. The mixture is then filtered through filter paper using a Buchner funnel. The filtrate is then fed through a Pope 2-inch diameter wiped film evaporator at approximately 30 grams/hour to distill the unreacted methyl esters. The evaporator operates at about 235° C. under about 0.05–0.08 mm Hg. The product is then collected from the evaporator and cooled to ambient temperature.

The finished solid polyol polyester has an octaester content of about 58.1%.

Fat Composition Preparation

Four (4) grams of this solid sucrose polyester and 96 grams of the liquid sucrose polyester hereinbefore described in Example I are mixed and heated until all the solids are dissolved. The mixture is then cooled back to room temperature at a rate of 33.3° F./min.

The resulting composition has a Solid Fat Content profile slope of −0.1% solids/°F. and is suitable for use as a food fat. It does not produce passive oil loss which would otherwise result if only the liquid sucrose polyester were to be used as a food fat. Also, as a result of the low solids levels used to prepare the fat composition and the relatively flat SFC profile slope, products made from this fat composition will not be waxy tasting.

EXAMPLE IV

Norchip potatoes are used which have been sliced to a thickness of about 0.052 inches (0.13 cm). The sliced potatoes are fried in a 5 pound batch fryer at a temperature of 365° F. (185° C. for about 3 minutes. Approximately 225 potato chips are fried in each of the fat compositions of Examples I, II and III.

Ingestion of these potato chips which contain the nondigestible fat compositions will not result in passive oil loss, and the potato chips are not unacceptably waxy tasting.

What is claimed is:

1. A nondigestible polyol fatty acid polyester having a complete melting point above about 25° C., said polyol polyester comprising:

(a) a polyol moiety containing at least 4 hydroxyl groups with at least 4 of said hydroxyl groups being esterified; and (b) ester groups consisting essentially of
  (i) at least about 15% $C_{20}$ or higher long chain saturated fatty acid radicals, and
  (ii) fatty-fatty acid radicals comprising a hydroxyl group-containing fatty acid radical wherein said hydroxyl group is itself esterified with a fatty acid radical;

the average molar ratio of said fatty-fatty acid radicals to said $C_{20}$ or higher long chain saturated fatty acid radicals ranging from about 0.1:7.9 to about 3:5.

2. The nondigestible polyol polyester of claim 1 wherein the polyol moiety has from 4 to 8 hydroxyl groups; the fatty-fatty acid radicals comprise fatty acid radicals of 12 to 22 carbon atoms with one or more hydroxyl groups and at least one fatty acid radical of 12 to 22 carbon atoms esterified onto at least one of said hydroxyl groups; and the long chain saturated fatty acid radicals contain from 20 to 26 carbon atoms.

3. The nondigestible polyol polyester of claim 2 wherein the molar ratio of fatty-fatty acid radicals to $C_{20}$–$C_{26}$ saturated fatty acid radicals ranges from about 1:7 to about 1.5:6.5 and at least about 85% of the hydroxyl groups of the polyol moiety are esterified.

4. The nondigestible polyol polyester of claim 3 wherein the polyol moiety is derived from sucrose.

5. The nondigestible polyol polyester of claim 4 wherein the hydroxyl group-containing fatty acid radical component of the fatty-fatty acid radicals consists essentially of ricinoleic acid radicals.

6. The nondigestible polyol polyester of claim 5 wherein the long chain saturated fatty acid radicals consist essentially of behenic acid radicals.

7. A nondigestible fat composition useful as a replacement for triglyceride fats or oils in foods, which composition has a Solid Fat Content profile slope between 70° F. and 98.6° F. of from 0 to about −0.75% solids/°F., and which composition comprises:

A. a liquid nondigestible oil having a complete melting point below about 37° C.; and B. nondigestible solid particles of polyol polyester dispersed in said oil in an amount sufficient to control passive oil loss upon ingestion of said composition, wherein said nondigestible solid particles have a complete melting point above about 37° C., and wherein the polyester material forming said particles comprises:
  (a) a polyol moiety containing at least 4 hydroxyl groups with at least 4 of the hydroxyl groups being esterified; and
  (b) ester groups consisting essentially of
    (i) at least about 15% $C_{20}$ or higher long chain saturated fatty acid radicals, and
    (ii) fatty-fatty acid radicals comprising a hydroxyl group-containing fatty acid radical wherein said hydroxyl group is itself esterified with a fatty acid radical;
  the average molar ratio of said fatty-fatty acid radicals to said $C_{20}$ or higher long chain saturated fatty acid radicals ranging from about 0.1:7.9 to about 3:5.

8. The nondigestible fat composition of claim 7 wherein the solid polyol polyester material comprises a polyol moiety which has from 4 to 8 hydroxyl groups; fatty-fatty acid radicals comprising fatty acid radicals of 12 to 22 carbon atoms containing one or more hydroxyl groups and at least one fatty acid radical of 12 to 22 carbon atoms esterified onto at least one of said hydroxyl groups; and long chain saturated fatty acid radicals containing from 20 to 26 carbon atoms.

9. The nondigestible fat composition of claim 8 which comprises from about 60% to about 99% liquid nondigestible oil and from about 1% to about 40% solid polyol polyester particles.

10. The nondigestible fat composition of claim 9 wherein in the polyol polyester particle material the molar ratio of fatty-fatty acid radicals to $C_{20}$–$C_{26}$ saturated fatty acid radicals ranges from about 1:7 to about 1.5:6.5 and at least about 85% of the hydroxyl groups of the polyol are esterified.

11. The nondigestible fat composition of claim 10 which comprises from about 85% to about 99% liquid sucrose fatty acid polyester and from about 1% to about 15% solid sucrose fatty acid polyester particles.

12. The nondigestible fat composition of claim 11 wherein in the sucrose fatty acid polyester particle material the hydroxyl group-containing fatty acid radical component of the fatty-fatty acid radicals consists essentially of ricinoleic acid radicals.

13. The nondigestible fat composition of claim 12 wherein in the sucrose fatty acid polyester particle material the long chain saturated fatty acid groups consist essentially of behenic acid radicals.

14. The nondigestible fat composition of claim 13 having a Solid Fat Content profile slope between 70° F. and 98.6° F. of from 0 to about −0.1% solids/°F.

15. The nondigestible fat composition of claim 14 wherein the nondigestible solid sucrose fatty acid polyester particles have a thickness of less than about 1 micron.

16. A thickened digestible oil product comprising:

A. from about 85% to about 99% of a digestible edible oil having a complete melting point below about 25° C.; and B. from about 1% to about 15% of solid nondigestible polyol polyester particles, wherein said particles have a complete melting point above about 37° C.; and wherein the polyol polyester material forming said particles comprises
  (a) a polyol moiety containing at least 4 hydroxyl groups with at least 4 of said hydroxyl groups being esterified; and
  (b) ester groups consisting essentially of
    (i) at least about 15% $C_{20}$ or higher long chain saturated fatty acid radicals, and
    (ii) fatty-fatty acid radicals comprising a hydroxyl group-containing fatty acid radical wherein said hydroxyl group is itself esterified with a fatty acid radical;
  the average molar ratio of said fatty-fatty acid radicals to said $C_{20}$ or higher long chain saturated fatty acid radicals ranging from about 0.1:7.9 to about 3:5.

17. The fat composition of claim 16 wherein the digestible oil is a triglyceride and wherein the solid polyol polyester particle material comprises a polyol moiety which has from 4 to 8 hydroxyl groups; fatty-fatty acid radicals comprising fatty acid radicals of 12 to 22 carbon atoms containing one or more hydroxyl groups and at least one fatty acid radical of 12 to 22 carbon atoms esterified onto at least one of said hydroxyl groups; and long chain saturated fatty acid radicals containing from 20 to 26 carbon atoms.

18. The fat composition of claim 17 wherein in the polyol polyester particle material the molar ratio of fatty-fatty acid radicals to long chain saturated fatty acid radicals ranges from 1:7 to 1.5:6.5 and at least about 85% of the hydroxyl groups of the polyol moiety are esterified.

19. The fat composition of claim 18 wherein the polyol moiety of the solid polyol polyester particle material is derived from sucrose.

20. The fat composition of claim 19 wherein in the sucrose polyol polyester particle material the hydroxyl group-containing fatty acid radical component of the fatty-fatty radicals consist essentially of ricinoleic acid radicals and the long chain saturated fatty acids consist essentially of behenic acid radicals.

* * * * *